(12) United States Patent  
Okabe et al.

(10) Patent No.: US 6,897,335 B2  
(45) Date of Patent: May 24, 2005

(54) PROCESS FOR PREPARATION OF 2-OXOCARBOXYLIC ACID ESTERS

(75) Inventors: Fumihiko Okabe, Niigata (JP); Masahiro Torihara, Niigata (JP); Yoshin Tamai, Niigata (JP)

(73) Assignee: Kuraray Co., Ltd., Kurashiki (JP)

( * ) Notice: Subject to any disclaimer, the term of this patent is extended or adjusted under 35 U.S.C. 154(b) by 0 days.

(21) Appl. No.: 10/480,802

(22) PCT Filed: Jun. 19, 2002

(86) PCT No.: PCT/JP02/06098

§ 371 (c)(1),  
(2), (4) Date: Dec. 19, 2003

(87) PCT Pub. No.: WO03/000638

PCT Pub. Date: Jan. 3, 2003

(65) Prior Publication Data

US 2004/0162441 A1 Aug. 19, 2004

(30) Foreign Application Priority Data

Jun. 20, 2001 (JP) .................... 2001-185891

(51) Int. Cl.[7] .................. C07C 69/66; C07C 69/76
(52) U.S. Cl. .................. 560/174; 560/60
(58) Field of Search .................. 560/60, 174

(56) References Cited

FOREIGN PATENT DOCUMENTS

| EP | 0 412 378 A1 | 2/1991 |
| EP | 11180932 | 7/1999 |
| EP | 11315052 | 11/1999 |

OTHER PUBLICATIONS

De Nooy et al, Synthesis, On the Use of Stable Organic Nitroxyl Radicals for the Oxidation of Primary and Secondary Alcohols, 1996, pp. 1153–1174.*

M. Robert Leanna, et al., Synthesis of α–Amino and α–Alkoxy Aldehydes via Oxoammonium Oxidation, Tetrahedron Letters, 1992, vol. 33, No. 35, pp. 5029 to 5032.

Chemical Abstracts of Japan, vol. 2000, No. 2, Feb. 29, 2000, XP002302646.

Chemical Abstracts of Japan, vol. 1999, No. 12, Oct. 29, 1999, XP–002302647.

* cited by examiner

*Primary Examiner*—Paul A. Zucker  
(74) *Attorney, Agent, or Firm*—Oblon, Spivak, McClelland, Maier & Neustadt, P.C.

(57) ABSTRACT

A process for the preparation of 2-oxocarboxylic acid esters represented by the following general formula (I), comprising by oxidizing a 2-hydroxycarboxylic acid ester represented by the following general formula (II) in the presence of a nitroxyl radical represented by the following general formula (III), a hypochlorite, a metal bromide and water with the pH of the reaction system being kept within the range of 5 to 7:

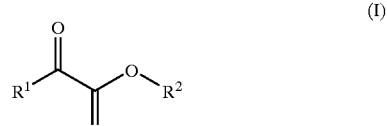

(I)

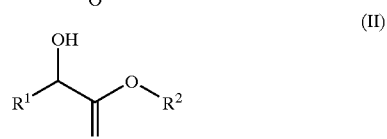

(II)

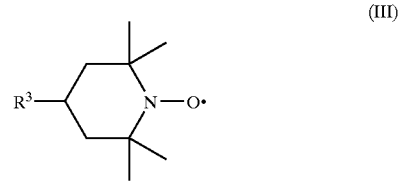

(III)

(I) (II) (III) wherein $R^1$ and $R^2$ are each independently an alkyl group, an alkenyl group, an alkynyl group, an aryl group or an aralkyl group, which each may be substituted with substituents; and $R^3$ is a hydrogen atom, an alkoxyl group, an aralkyloxy group, an acyloxy group or a hydroxyl group.

2 Claims, No Drawings

PROCESS FOR PREPARATION OF 2-OXOCARBOXYLIC ACID ESTERS

TECHNICAL FIELD

The present invention relates to a process for the preparation of 2-oxocarboxylic acid esters suitable for use as an intermediate in the synthesis of pharmaceutical products, such as (S)-α-ethyl-2-oxo-1-pyrrolidine acetamide, an antiepileptic agent (See, Japanese Patent Laid-Open Publication No. Sho 60-252461).

BACKGROUND ART

Several methods are known for the preparation of 2-oxocarboxylic acid esters. Among such methods are (1) oxidation of an acetylene compound with osmium oxide (See, Journal of Organic Chemistry. 43, 21 (1978); 4245); (2) reaction of an oxalic acid diester with an alkyl aluminum (See, German Patent Publication No. 2151867); (3) oxidative dehydrogenation of a 2-hydroxycarboxylic acid ester in gas phase (See, Japanese Patent Laid-Open Publication No. Hei 5-255190 and Japanese Patent Laid-Open Publication No. Hei 8-34762); (4) oxidation of a 2-hydroxycarboxylic acid ester with chlorine under light irradiation (See, Japanese Patent Laid-Open Publication No. Hei 11-228502); (5) oxidation of a 2-hydroxycarboxylic acid ester with a hypochlorite in a hydrophobic solvent in the presence of a hindered secondary amine under acidic condition of pH 6 or lower (See, Japanese Patent Laid-Open Publication No. Hei 11-315052); (6) oxidation of a 2-hydroxycarboxylic acid ester with a hypochlorous acid in the presence of a catalytic amount of a nitroxyl radical in a solvent substantially consisting of a halogenated hydrocarbon (See, Japanese Patent Laid-Open Publication No. Hei 3-58956); and (7) oxidation of a 2-hydroxycarboxylic acid ester with sodium hypochlorite in the presence of a nitroxyl radical and sodium bromide (See, Tetrahedron Letters. 33, 35 (1992); 5033).

These approaches, however, all have their respective disadvantages: the process (1) involves the use of osmium oxide which is harmful to human being; the process (2) involves the use of an alkyl aluminum, a material difficult to handle on an industrial scale; the process (3), which is a gas phase reaction, and the process (4), which involves light irradiation, each requires special facilities; in the process (5), the hindered secondary amine must be activated prior to use by treatment with a peracid, which is difficult to handle; the process (6) involves the use of a halogenated hydrocarbon solvent, which is harmful to environment; and by the process (7), the desired 2-oxocarboxylic acid ester can be produced only at low yield. Thus, none of these approaches is an industrially advantageous process for the preparation of 2-oxocarboxylic acid esters.

Accordingly, it is an objective of the present invention to provide an industrially advantageous process of 2-oxocarboxylic acid esters that allows efficient, simple preparation of the compounds.

DISCLOSURE OF THE INVENTION

According to the present invention, the above-described objective is achieved by providing a process for the preparation of 2-oxocarboxylic acid esters represented by the following general formula (I):

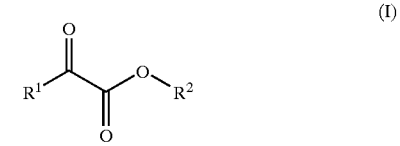

wherein $R^1$ and $R^2$ are each independently an alkyl group, an alkenyl group, an alkynyl group, an aryl group or an aralkyl group, which each may be substituted with substituents, the compound is referred to as 2-oxocarboxylic acid ester (I), comprising oxidizing a 2-hydroxycarboxylic acid ester represented by the following general formula (II):

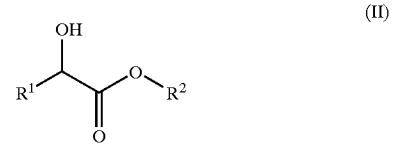

wherein $R^1$ and $R^2$ are as defined above, the compound is referred to as 2-hydroxycarboxylic acid ester (II), in the presence of a nitroxyl radical represented by the following general formula (III):

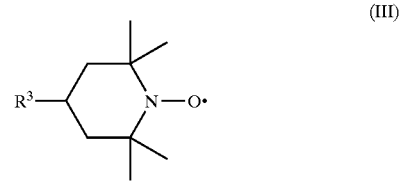

wherein $R^3$ is a hydrogen atom, an alkoxyl group, an aralkyloxy group, an acyloxy group or a hydroxyl group, the compound is referred to nitroxyl radical (III), a hypochlorite, a metal bromide and water with the pH of the reaction system being kept within the range of 5 to 7.

BEST MODE FOR CARRYING OUT THE INVENTION

The alkyl group that $R^1$ and $R^2$ independently represent in the general formulae above is preferably an alkyl group having 1 to 8 carbon atoms, such as methyl, ethyl, n-propyl, isopropyl, n-butyl, isobutyl, sec-butyl, tert-butyl, n-pentyl, isopentyl, neopentyl, 3-pentyl, n-hexyl, 3-methyl-1-pentyl, n-heptyl, 4-heptyl, n-octyl, cyclopropyl, cyclobutyl, cyclopentyl and cyclohexyl. The alkenyl group that $R^1$ and $R^2$ independently represent in the general formulae above is preferably an alkenyl group having 2 to 8 carbon atoms, such as vinyl, allyl, propenyl, butenyl and octenyl. The alkynyl group that $R^1$ and $R^2$ independently represent in the general formulae above is preferably an alkynyl group having 2 to 8 carbon atoms, such as ethynyl, propynyl, butynyl and octynyl. Each of the alkyl, alkenyl and alkynyl groups may be substituted with substituents. Examples of such substituents include halogen atom such as fluorine atom, chlorine atom, bromine atom and iodine atom; alkoxyl group having 1 to 4 carbon atoms such as methoxy, ethoxy, propoxy and butoxy; acyloxy group having 2 to 11 carbon atoms such as acetoxy and benzoyloxy; and nitro group.

The aryl group that $R^1$ and $R^2$ independently represent in the general formulae above is preferably an aryl group having 6 to 10 carbon atoms, such as phenyl and naphthyl.

The aralkyl group that $R^1$ and $R^2$ independently represent in the general formulae above is preferably an aralkyl group consisting of an alkyl group having 1 to 6 carbon atoms and an aryl group having 6 to 10 carbon atoms, such as benzyl, 1-phenylethyl, 2-phenylethyl, 1-phenylpropyl, 3-phenylpropyl, 4-phenylbutyl, 2-phenylhexyl, naphthylmethyl and 3-naphthylbutyl. Each of the aryl and aralkyl groups may be substituted with substituents. Preferred examples of such substituents include halogen atom such as fluorine atom, chlorine atom, bromine atom and iodine atom; alkyl group having 1 to 4 carbon atoms such as methyl, ethyl, propyl and butyl; aryl group having 6 to 10 carbon atoms such as phenyl, 4-methylphenyl and naphthyl; alkoxyl group having 1 to 4 carbon atoms such as methoxy, ethoxy, propoxy and butoxy; acyloxy group having 2 to 11 carbon atoms such as acetoxy and benzoyloxy; and nitro group.

The alkoxyl group that $R^3$ represents in the general formula above is preferably an alkoxyl group having 1 to 8 carbon atoms, such as methoxy, ethoxy, propoxy, butoxy, hexyloxy and octyloxy. The aralkyloxy group that $R^3$ represents in the general formula above is preferably an aralkyloxy group consisting of an alkyl group having 1 to 6 carbon atoms and an aryl group having 6 to 10 carbon atoms, such as phenylethyloxy and benzyloxy. The acyloxy group that $R_3$ represents in the general formula above is preferably an acyloxy group having 2 to 7 carbon atoms, such as acetoxy, propionyloxy and benzoyloxy.

Examples of the 2-hydroxycarboxylic acid ester (II) for use in the present invention include methyl mandelate, ethyl mandelate, ethyl 2-hydroxy-2-(4-methoxycarbonylphenyl) acetate, methyl 2-hydroxypropionate, ethyl 2-hydroxypropionate, methyl 2-hydroxy-3-phenylpropionate, methyl 2-hydroxybutanoate, isopropyl 2-hydroxybutanoate, n-butyl 2-hydroxybutanoate, methyl 2-hydroxy-3-methylbutanoate, ethyl 2-hydroxy-3-phenylbutanoate, ethyl 2-hydroxy-4-(4-chlorophenyl) butanoate, methyl 4-acetoxy-2-hydroxybutanoate, methyl 2-hydroxypentanoate, ethyl 2-hydroxypentanoate, methyl 2-hydroxy-3-phenylpentanoate, isopropyl 2-hydroxy-5-(2-methoxyphenyl)pentanoate, tert-butyl 4-chloro-2-hydroxy-5-(2-naphthyl)hexanoate, n-butyl 4-fluoro-2-hydroxy-4-(4-methylphenyl)octanoate, methyl 2-hydroxynonanoate, ethyl 2-hydroxynonanoate, ethyl 3-bromo-2-hydroxy-5-nitrononanoate, ethyl 2-hydroxy-3-butenoate and methyl 2-hydroxy-4-pentynoate.

Examples of the nitroxyl radical (III) for use in the present invention include 2,2,6,6-tetramethylpiperidine-1-oxy, 4-methoxy-2,2,6,6-tetramethylpiperidine-1-oxy, 4-benzyloxy-2,2,6,6-tetramethylpiperidine-1-oxy, 4-acetoxy-2,2,6,6-tetramethylpiperidine-1-oxy, 4-benzoyloxy-2,2,6,6-tetramethylpiperidine-1-oxy and 4-hydroxy-2,2,6,6-tetramethylpiperidine-1-oxy. Of these, 4-acetoxy-2,2,6,6-tetramethylpiperidine-1-oxy is particularly preferred. The nitroxyl radical (III) is preferably used in an amount of 0.001 to 1.0 molar equivalents of the 2-hydroxycarboxylic acid ester (II), and more preferably in an amount of 0.001 to 0.2 molar equivalents of the 2-hydroxycarboxylic acid ester (II) from economical point of view.

Examples of the hypochlorite for use in the present invention include sodium hypochlorite, potassium hypochlorite and calcium hypochlorite (high test hypochlorite). Hypochlorites are generally used in the form of aqueous solution. Of these hypochlorites, sodium hypochlorite is particularly preferred since it is obtained at a low cost in the form of an aqueous solution containing 12 to 13% by mass of the compound and is easy to handle. When it is desired to use an aqueous solution of sodium hypochlorite, commercially available products may be used either directly or after dilution. When it is desired to use hypochlorite available in the form of solid, such as high test hypochlorite, it may be used directly or it may be dissolved in water to form an aqueous solution containing 5 to 20% by mass of the compound. The hypochlorite is preferably used in an amount of 1 to 10 molar equivalents, more preferably 1 to 4 molar equivalents, of the 2-hydroxycarboxylic acid ester (II).

Examples of the metal bromide for use in the present invention include alkali metal bromides, such as lithium bromide, sodium bromide and potassium bromide; and alkaline earth metal bromides, such as magnesium bromide and barium bromide. The metal bromide is preferably used in an amount of 0.001 to 10.0 molar equivalents of the 2-hydroxycarboxylic acid ester (II), and more preferably in an amount of 0.002 to 0.3 molar equivalents of the 2-hydroxycarboxylic acid ester (II) in the viewpoint of economy and selectivity of the reaction.

While water may be used in any amount in the reaction of the present invention, it is preferably used in an amount of 0.1 to 500 times (by mass), preferably 0.5 to 100 times (by mass) the amount of the metal bromide.

Preferably, the reaction is carried out in the presence of a solvent. Such solvent may be any solvent that does not affect the reaction, including esters such as methyl acetate, ethyl acetate, propyl acetate, butyl acetate, methyl propionate and ethyl propionate; aliphatic hydrocarbons such as pentane, hexane, heptane and cyclohexane; and aromatic hydrocarbons such as benzene, toluene and xylene. These solvents may be used either independently or as a mixture of two or more. The solvent is preferably used in an amount of 0.1 to 100 times (by mass) the amount of the 2-hydroxycarboxylic acid ester (II), and more preferably in an amount of 1 to 20 times (by mass) the amount of the 2-hydroxycarboxylic acid ester (II) in terms of economy and readiness in post-treatment.

While the reaction of the present invention is typically carried out in a pH range of 5 to 7, it is preferably carried out in a pH range of 5 to 6. If the pH of the reaction system is below 5, the nitroxyl radical (III) catalyst will lose activity and the reaction will not proceed. While if the pH of the reaction system is above 7, the 2-oxocarboxylic acid ester (I), the reaction product, will be hydrolyzed, resulting in a reduced yield and purity of the product.

While the pH of the reaction system may be adjusted by any proper technique, it may be adjusted for example by gradually adding an acid to the reaction system while the pH is monitored. The acid in such a case must be of a type that does not affect the reaction. The pH may also be adjusted by including a buffer in the reaction system prior to the reaction. Examples of the acid suitable for use in the former technique include mineral acids such as hydrochloric acid, sulfuric acid, nitric acid, boric acid and phosphoric acid; organic acids such as acetic acid, propionic acid and p-toluenesulfonic acid; phosphates such as potassium dihydrogen phosphate and sodium dihydrogen phosphate; and potassium hydrogen phthalate. These acids may be used directly, or it may be dissolved in or diluted with water. Of these acids, mineral acids or phosphates are particularly preferred since the adjustment of the pH is particularly easy with the use of these acids.

Preferably, the reaction is carried out at a temperature of 0 to 80° C., and more preferably at a temperature of 0 to 50°

C. The reaction is typically carried out over a time period of 30 minutes to 50 hours while the reaction time may vary depending on the types of the 2-hydroxycarboxylic acid ester (II), the hypochlorite, the nitroxyl radical (III), the metal bromide and the solvent, as well as their amounts and the reaction temperature.

The reaction process may be any proper process. In a preferred reaction process, the 2-hydroxycarboxylic acid ester (II), the nitroxyl radical (III), the metal bromide, water, and when necessary, the solvent, are mixed with each other and while the reaction system is maintained at a predetermined temperature and within a pH range of 5 to 7, the hypochlorite is added to the reaction mixture in small portions.

The 2-oxocarboxylic acid ester (I), the desired product of the present invention, can be isolated/purified from the resulting reaction mixture by the use of techniques commonly used in the isolation/purification of organic compounds. In a preferred example, a reductant, such as sodium thiosulfate, is added to the reaction mixture to decompose the remaining hypochlorite, and the aqueous and the organic layers are separated. The aqueous layer is then extracted with an organic solvent such as ethyl acetate. The extract is added to the organic layer, and the combined organic layer is concentrated. The nitroxyl radical (III) and other high-boiling-point components are then removed by thin-film distillation and the resulting distillate is purified by distillation, column chromatography or other purification means.

The 2-hydroxycarboxylic acid ester (II), such as methyl 2-hydroxybutanoate, to use as the starting material of the process of the present invention can be obtained, for example, in the following manner: a cyanohydrin is amidated with water and sulfuric acid, followed by the addition of an alcohol to esterify the product. While an aqueous alcohol is continuously fed to the reaction mixture, the hydroxycarboxylic acid ester, as it is generated, is collected by distillation (See, Japanese Patent Laid-Open Publication No. Hei 6-247896).

The present invention will now be described in detail with reference to Examples, which are provided by way of example only and are not intended to limit the scope of the invention in any way.

EXAMPLE 1

10 g (84.7 mmol) of methyl 2-hydroxybutanoate, 0.09 g (0.42 mmol) of 4-acetoxy-2,2,6,6-tetramethylpiperidine-1-oxy, 0.87 g (8.47 mmol) of sodium bromide, 11 g of water and 43.4 g of ethyl acetate were placed in a 200 ml four-necked flask equipped with two dropping funnels, a thermometer, a pH meter and a stirrer. The temperature inside was lowered to 0 to 10° C. With the internal temperature kept below 10° C., 56.2 g (97.4 mmol) of 13% (by mass) aqueous solution of sodium hypochlorite was continuously added dropwise to the mixture. To prevent the pH of the reaction system from becoming basic during the addition of the aqueous solution of sodium hypochlorite, 20% (by mass) aqueous solution of phosphoric acid was also added dropwise to the mixture to maintain the pH of the reaction system within a range of 5 to 6. Following the addition of the aqueous solution of sodium hypochlorite, the reaction mixture was stirred for additional 1 hour. The organic and the aqueous layers were separated and were subjected to gas chromatography analysis using internal standard technique. The results of the analysis indicated that 99.9% of methyl 2-hydroxybutanoate was converted to produce 9.45 g of methyl 2-oxobutanoate (96.0% yield).

The aqueous layer was extracted with 21.7 g of ethyl acetate. The resulting organic layer was added to the organic layer obtained previously and the combined organic layer was concentrated. The resulting residue was purified by thin-film distillation and the distillate was further distilled to obtain 8.71 g of methyl 2-oxobutanoate (97.6% purity and 86.4% isolated yield).

EXAMPLE 2

10 g (84.7 mmol) of methyl 2-hydroxybutanoate, 0.09 g (0.42 mmol) of 4-acetoxy-2,2,6,6-tetramethylpiperidine-1-oxy, 0.87 g (8.47 mmol) of sodium bromide, 11 g of water and 43.4 g of ethyl acetate were placed in a 200 ml four-necked flask equipped with two dropping funnels, a thermometer, a pH meter and a stirrer. The temperature inside was lowered to 0 to 10° C. With the internal temperature kept below 10° C., 56.2 g (97.4 mmol) of 13% (by mass) aqueous solution of sodium hypochlorite was continuously added dropwise to the mixture. To prevent the pH of the reaction system from becoming basic during the addition of the aqueous solution of sodium hypochlorite, 20% (by mass) aqueous solution of phosphoric acid was also added dropwise to the mixture to maintain the pH of the reaction system within a range of 6 to 6.5. Following the addition of the aqueous solution of sodium hypochlorite, the reaction mixture was stirred for additional 1 hour. The organic and the aqueous layers were separated and were subjected to gas chromatography analysis using internal standard technique. The results of the analysis indicated that 99.9% of methyl 2-hydroxybutanoate was converted to produce 9.21 g of methyl 2-oxobutanoate (93.7% yield).

EXAMPLE 3

10 g (84.7 mmol) of methyl 2-hydroxybutanoate, 0.09 g (0.42 mmol) of 4-acetoxy-2,2,6,6-tetramethylpiperidine-1-oxy, 0.87 g (8.47 mmol) of sodium bromide, 11 g of water and 43.4 g of ethyl acetate were placed in a 200 ml four-necked flask equipped with two dropping funnels, a thermometer, a pH meter and a stirrer. The temperature inside was lowered to 0 to 10° C. With the internal temperature kept below 10° C., 56.2 g (97.4 mmol) of 13% (by mass) aqueous solution of sodium hypochlorite was continuously added dropwise to the mixture. To prevent the pH of the reaction system from becoming basic during the addition of the aqueous solution of sodium hypochlorite, 20% (by mass) aqueous solution of phosphoric acid was also added dropwise to the mixture to maintain the pH of the reaction system within a range of 6.5 to 7. Following the addition of the aqueous solution of sodium hypochlorite, the reaction mixture was stirred for additional 1 hour. The organic and the aqueous layers were separated and were subjected to gas chromatography analysis using internal standard technique. The results of the analysis indicated that 99.9% of methyl 2-hydroxybutanoate was converted to produce 8.96 g of methyl 2-oxobutanoate (91.0% yield).

COMPARATIVE EXAMPLE 1

10 g (84.7 mmol) of methyl 2-hydroxybutanoate, 0.09 g (0.42 mmol) of 4-acetoxy-2,2,6,6-tetramethylpiperidine-1-oxy, 0.87 g (8.47 mmol) of sodium bromide, 11 g of water and 43.4 g of ethyl acetate were placed in a 200 ml four-necked flask equipped with two dropping funnels, a thermometer, a pH meter and a stirrer. The temperature inside was lowered to 0 to 10° C. With the internal temperature kept below 10° C., 56.2 g (97.4 mmol) of 13% (by mass) aqueous solution of sodium hypochlorite was continuously added dropwise to the mixture. To prevent the pH of the reaction system from becoming basic during the addition of the aqueous solution of sodium hypochlorite, 20% (by mass) aqueous solution of phosphoric acid was also added dropwise to the mixture to maintain the pH of the reaction system within a range of 3 to 4. Following the addition of the aqueous solution of sodium hypochlorite, the reaction mixture was stirred for additional 1 hour. The organic and the aqueous layers were separated and were subjected to gas chromatography analysis using internal standard technique. The results of the analysis indicated that 44.9% of methyl 2-hydroxybutanoate was converted to produce 4.30 g of methyl 2-oxobutanoate (43.6% yield).

COMPARATIVE EXAMPLE 2

10 g (84.7 mmol) of methyl 2-hydroxybutanoate, 0.09 g of (0.42 mmol) 4-acetoxy-2,2,6,6-tetramethylpiperidine-1-oxy, 0.87 g (8.47 mmol) of sodium bromide, 11 g of water and 43.4 g of ethyl acetate were placed in a 200 ml four-necked flask equipped with two dropping funnels, a thermometer, a pH meter and a stirrer. The temperature inside was lowered to 0 to 10° C. With the internal temperature kept below 10° C., 56.2 g (97.4 mmol) of 13% (by mass) aqueous solution of sodium hypochlorite was continuously added dropwise to the mixture. To prevent the pH of the reaction system from becoming basic during the addition of the aqueous solution of sodium hypochlorite, 20% (by mass) aqueous solution of phosphoric acid was also added dropwise to the mixture to maintain the pH of the reaction system within a range of 4 to 4.5. Following the addition of the aqueous solution of sodium hypochlorite, the reaction mixture was stirred for additional 1 hour. The organic and the aqueous layers were separated and were subjected to gas chromatography analysis using internal standard technique. The results of the analysis indicated that 40.6% of methyl 2-hydroxybutanoate was converted to produce 3.82 g of methyl 2-oxobutanoate (38.9% yield).

COMPARATIVE EXAMPLE 3

10 g (84.7 mmol) of methyl 2-hydroxybutanoate, 0.09 g of (0.42 mmol) 4-acetoxy-2,2,6,6-tetramethylpiperidine-1-oxy, 0.87 g (8.47 mmol) of sodium bromide, 11 g of water and 43.4 g of ethyl acetate were placed in a 200 ml four-necked flask equipped with two dropping funnels, a thermometer, a pH meter and a stirrer. The temperature inside was lowered to 0 to 10° C. With the internal temperature kept below 10° C., 56.2 g (97.4 mmol) of 13% (by mass) aqueous solution of sodium hypochlorite was continuously added dropwise to the mixture. To prevent the pH of the reaction system from becoming basic during the addition of the aqueous solution of sodium hypochlorite, 20% (by mass) aqueous solution of phosphoric acid was also added dropwise to the mixture to maintain the pH of the reaction system within a range of 4.5 to 5. Following the addition of the aqueous solution of sodium hypochlorite, the reaction mixture was stirred for additional 1 hour. The organic and the aqueous layers were separated and were subjected to gas chromatography analysis using internal standard technique. The results of the analysis indicated that 73.9% of methyl 2-hydroxybutanoate was converted to produce 6.90 g of methyl 2-oxobutanoate (70.2% yield).

COMPARATIVE EXAMPLE 4

10 g (84.7 mmol) of methyl 2-hydroxybutanoate, 0.09 g (0.42 mmol) of 4-acetoxy-2,2,6,6-tetramethylpiperidine-1-oxy, 0.87 g (8.47 mmol) of sodium bromide, 11 g of water and 43.4 g of ethyl acetate were placed in a 200 ml four-necked flask equipped with two dropping funnels, a thermometer, a pH meter and a stirrer. The temperature inside was lowered to 0 to 10° C. With the internal temperature kept below 10° C., 56.2 g (97.4 mmol) of 13% (by mass) aqueous solution of sodium hypochlorite was continuously added dropwise to the mixture. During the addition of the aqueous solution of sodium hypochlorite, 20% (by mass) aqueous solution of phosphoric acid was also added dropwise to the mixture to adjust the pH of the reaction system to a range of 7 to 8. Following the addition of the aqueous solution of sodium hypochlorite, the reaction mixture was stirred for additional 1 hour. The organic and the aqueous layers were separated and were subjected to gas chromatography analysis using internal standard technique. The results of the analysis indicated that 92.9% of methyl 2-hydroxybutanoate was converted to produce 7.30 g of methyl 2-oxobutanoate (74.3% yield).

COMPARATIVE EXAMPLE 5

10 g (84.7 mmol) of methyl 2-hydroxybutanoate, 0.09 g (0.42 mmol) of 4-acetoxy-2,2,6,6-tetramethylpiperidine-1-oxy, 11 g of water and 43.4 g of ethyl acetate were placed in a 200 ml four-necked flask equipped with two dropping funnels, a thermometer, a pH meter and a stirrer. The temperature inside was lowered to 0 to 10° C. With the internal temperature kept below 10° C., 56.2 g (97.4 mmol) of 13% (by mass) aqueous solution of sodium hypochlorite was continuously added dropwise to the mixture. To prevent the pH of the reaction system from becoming basic during the addition of the aqueous solution of sodium hypochlorite, 20% (by mass) aqueous solution of phosphoric acid was also added dropwise to the mixture to maintain the pH of the reaction system within a range of 5 to 6. Following the addition of the aqueous solution of sodium hypochlorite, the reaction mixture was stirred for additional 1 hour. The organic and the aqueous layers were separated and were subjected to gas chromatography analysis using internal standard technique. The results of the analysis indicated that 87.0% of methyl 2-hydroxybutanoate was converted to produce 7.63 g of methyl 2-oxobutanoate (89.1% yield).

INDUSTRIAL APPLICABILITY

The present invention allows efficient, simple and industrially advantageous preparation of 2-oxocarboxylic acid esters (I).

What is claimed is:

1. A process for the preparation of 2-oxocarboxylic acid esters represented by the following general formula (I):

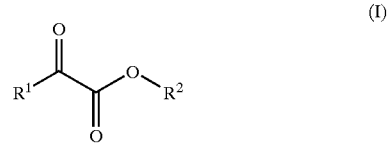

wherein $R^1$ and $R^2$ are each independently an alkyl group, an alkenyl group, an alkynyl group, an aryl group or an aralkyl group, which each may be substituted with substituents, comprising oxidizing a 2-hydroxycarboxylic acid ester represented by the following general formula (II):

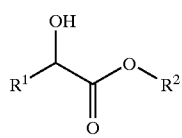

(II)

wherein $R^1$ and $R^2$ are as defined above, in the presence of a nitroxyl radical represented by the following general formula (III):

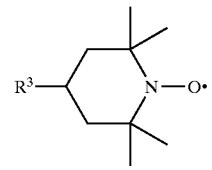

(III)

wherein $R^3$ is a hydrogen atom, an alkoxyl group, an aralkyloxy group, an acyloxy group or a hydroxyl group, a hypochlorite, a metal bromide and water with the pH of the reaction system being kept within the range of 5 to 7.

2. The process according to claim 1, wherein the pH of the reaction system is kept within the range of 5 to 6.

* * * * *